(12) United States Patent
Melhem et al.

(10) Patent No.: US 9,445,835 B2
(45) Date of Patent: Sep. 20, 2016

(54) CIRCUMCISION DEVICE

(76) Inventors: Milad Melhem, Bankstown (AU); Rachid Tabba, Belmore (AU)

( * ) Notice: Subject to any disclaimer, the term of this patent is extended or adjusted under 35 U.S.C. 154(b) by 0 days.

(21) Appl. No.: 13/389,793

(22) PCT Filed: Jul. 30, 2010

(86) PCT No.: PCT/AU2010/000966
§ 371 (c)(1),
(2), (4) Date: Apr. 10, 2012

(87) PCT Pub. No.: WO2011/017737
PCT Pub. Date: Feb. 17, 2011

(65) Prior Publication Data
US 2012/0203243 A1    Aug. 9, 2012

(30) Foreign Application Priority Data
Aug. 13, 2009    (AU) .............................. 2009903801

(51) Int. Cl.
*A61B 17/32* (2006.01)
*A61B 17/326* (2006.01)

(52) U.S. Cl.
CPC .................................. *A61B 17/326* (2013.01)

(58) Field of Classification Search
CPC .................................................... A61B 17/326
USPC ................................................ 606/118, 139
See application file for complete search history.

(56) References Cited

U.S. PATENT DOCUMENTS

| | | | |
|---|---|---|---|
| 3,056,407 A | | 10/1962 | Kariher et al. |
| 5,797,921 A | * | 8/1998 | Cimini et al. ............... 606/118 |
| 5,860,988 A | * | 1/1999 | Rawlings ............. A61B 17/326 |
| | | | 606/118 |
| 7,303,567 B1 | * | 12/2007 | Smith .......................... 606/118 |
| 2006/0122626 A1 | * | 6/2006 | Duel .................... A61B 17/326 |
| | | | 606/118 |
| 2008/0021482 A1 | * | 1/2008 | Tomlinson ..................... 606/118 |
| 2008/0154283 A1 | * | 6/2008 | Shang ........................... 606/118 |
| 2011/0098718 A1 | * | 4/2011 | Shang ........................... 606/118 |

FOREIGN PATENT DOCUMENTS

| | | |
|---|---|---|
| CN | 2441443 Y | 8/2001 |
| CN | 2508709 Y | 9/2002 |
| CN | 2899717 Y | 5/2007 |

OTHER PUBLICATIONS

International Preliminary Report on Patentability, dated Jul. 6, 2011 in corresponding PCT/AU2010/000966 application.
Bode, C.O., et al., "Penile injuries from proximal migration of the plastibell circumcision ring," Journal of Pediatric Urology, 2009, 5 pages.

(Continued)

*Primary Examiner* — Corrine McDermott
*Assistant Examiner* — Sarah Simpson
(74) *Attorney, Agent, or Firm* — Kilpatrick Townsend & Stockton LLP

(57) ABSTRACT

A circumcision device (10) including a proximal end (16), a distal end (18), an inner recess (30) and an outer surface. The inner recess (30) opens from the proximal end (16) and is adapted to receive substantially all of a glans of a penis therein. The outer surface includes a plurality of indicators (26) spaced apart from the proximal end (16). In use, a foreskin is pulled over the outer surface until the foreskin reaches a predetermined one of the indicators (26), thereby providing a visual guide to the level of circumcision.

16 Claims, 6 Drawing Sheets

(56) References Cited

OTHER PUBLICATIONS

Cilento, Bartley G. et al., "Plastibell® Complications Revisited," Clinical Pediatrics, 1999, No. 38, pp. 239-242.
Morris, Brian J. et al., "Male Circumcision: An Appraisal of Current Instrumentation," Biomedical Engineering—From Theory to Applications, Prof. Reza Fazel (Ed.), 2011, ISBN: 978-953-307-637-9, chapter 14, pp. 316-354.
Mousavi, Seyed Abdollah et al., "Circumcision Complications Associated with the Plastibell Device and Conventional Dissection Surgery: A Trial of 586 Infants of Ages up to 12 Months," Advances in Urology, 2008, 5 pages.
Smith, A.W., et al., "Management of Plastibell circumcision ring migration and glans penis incarceration," Journal of Pediatric Surgery Case Reports, 2013, No. 1, pp. 186-188.

\* cited by examiner

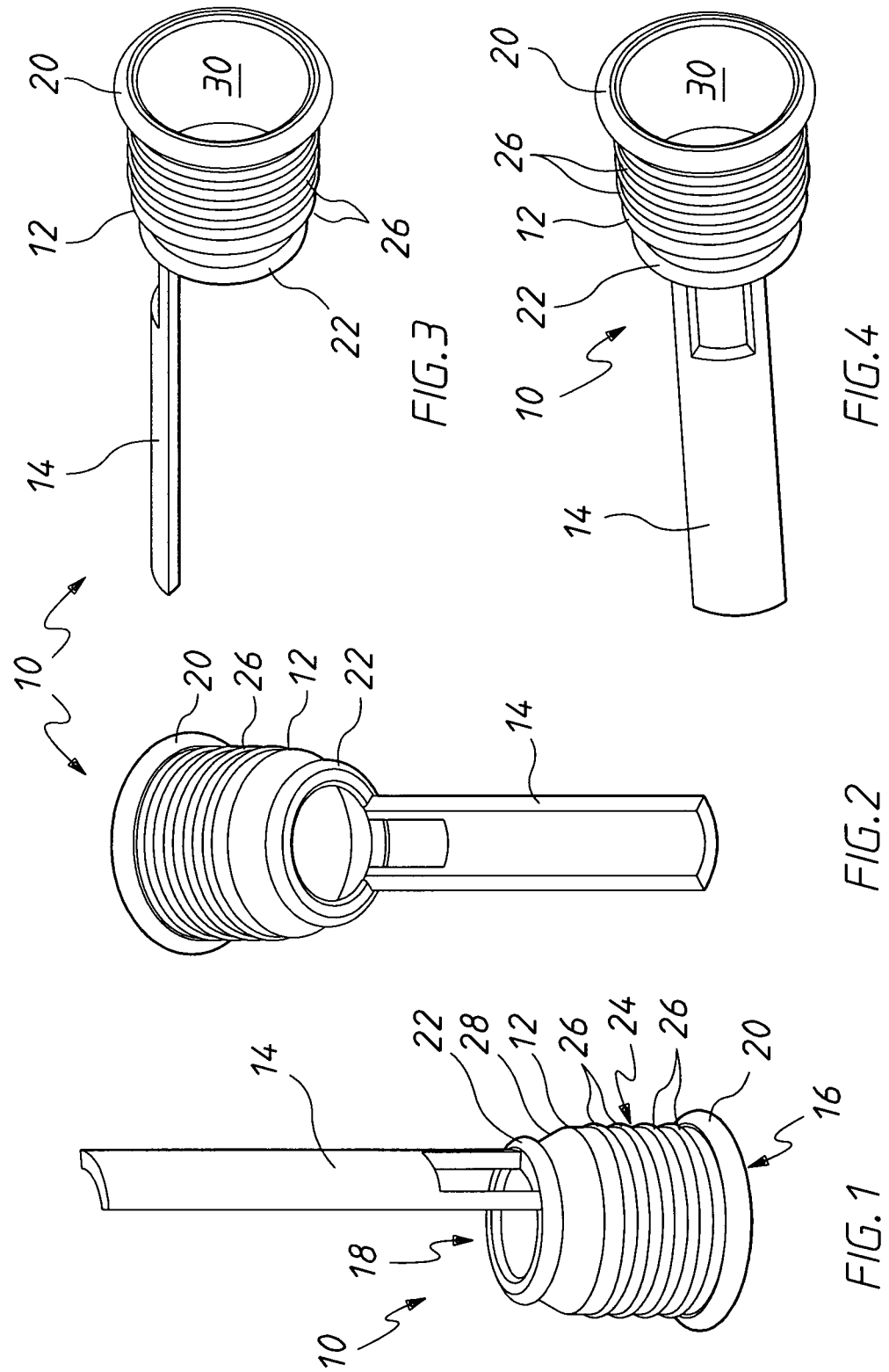

CIRCUMCISION DEVICE

CROSS-REFERENCES TO RELATED APPLICATIONS

This application is a National Stage of International Application No. PCT/AU2010/000966 filed Jul. 30, 2010, which claims the benefit of Australian Provisional Application No. 2009903801, filed Aug. 13, 2009, the disclosures of which are all incorporated herein by reference.

FIELD OF THE INVENTION

The present invention relates to a circumcision device and a method of circumcision. The circumcision device has been developed for use in circumcising male infants and children and will be described hereinafter with reference to this application.

BACKGROUND OF THE INVENTION

The most wide spread single use circumcision device currently in use is marketed under the trademark PLASTIBELL. The PLASTIBELL device has a domed plastic ring with a frangible handle, and is available in six sizes. To use the PLASTIBELL device, the adhesions between the glans and foreskin are divided with a probe and the foreskin is then cut longitudinally to allow it to be retracted to expose the glans. The appropriate sized PLASTIBELL device is then selected and the ring applied to the head of the penis. The ring is then covered over by the foreskin and a ligature is tied firmly around the foreskin, which crushes the skin against the ring. The excess skin protruding beyond the ring is then trimmed off. To end the circumcision procedure, the handle is broken off the ring. The ring typically falls off in three to seven days leaving a circumferential wound that heals over the following week.

The PLASTIBELL device has several disadvantages. Firstly, the glans is unprotected during the circumcision procedure. As the ligature which is used to secure the foreskin must be tight, any slippage can cause injury to the glans.

Secondly, once the PLASTIBELL device is in place and the foreskin is clamped thereto, it is extremely difficult, due to a lack of visibility, to determine where the ring begins and where the glans ends. This is due to the foreskin covering the majority of the ring. This makes it difficult for the surgeon to perform the circumcision as it leads to difficulty in locating the area in which to tie the ligature. This in turn may lead to injury such as urethrocutaneous fistulae, extensive skin loss, dysuria, or ischemic necrosis.

Thirdly, once the PLASTIBELL device is in place, it governs how much of the foreskin may be removed. This is because the glans is pressed up against the ring, which blocks the glans from moving through the ring any further. This can result in only a limited, often less than ideal, amount of foreskin being able to be removed.

OBJECT OF THE INVENTION

It is the object of the present invention to substantially overcome or at least ameliorate one or more of the above disadvantages.

SUMMARY OF THE INVENTION

Accordingly, in a first aspect, the present invention provides a circumcision device including:
a proximal end;
a distal end;
an inner recess opening from the proximal end and adapted to receive substantially all of a glans of a penis therein; and
an outer surface including a plurality of indicators spaced apart from the proximal end,
wherein, in use, a foreskin is pulled over the outer surface until the foreskin reaches a predetermined one of the indicators, thereby providing a visual guide to the level of circumcision.

The device preferably includes a first outwardly protruding peripheral flange about the proximal end. The device preferably also includes a second outwardly protruding peripheral flange about the distal end. The first flange is preferably larger in diameter than the second flange.

In a second aspect, the present invention provides a circumcision device including:
a proximal end;
a distal end;
an inner recess opening from the proximal end and adapted to receive substantially all of a glans of a penis therein; and
a first outwardly protruding peripheral flange about the proximal end.

The device preferably also includes a second outwardly protruding peripheral flange about the distal end. The first flange is preferably larger in diameter than the second flange.

The device preferably includes a generally cylindrical body, most preferably with a tapered part adjacent the distal end. The device preferably includes a handle, frangibly attached to the body, most preferably adjacent the distal end.

The indicators are preferably formed on the exterior of the body.

The recess is preferably formed within the body. The recess is preferably inwardly concave.

The indicators are preferably in the form of outwardly protruding peripheral ribs. The ribs are preferably longitudinally, most preferably equally, spaced apart. The device preferably includes four or five ribs.

In a third aspect, the present invention provides a method of circumcision including the following steps:
inserting substantially all of a glans of a penis into an inner recess in a proximal end of a circumcision device;
pulling a foreskin over an outer surface of the circumcision device, until the foreskin reaches a predetermined one of a plurality of indicators, spaced from the proximal end, corresponding to a selected level of circumcision; and
tying a ligature around the foreskin adjacent the predetermined one of said indicators.

BRIEF DESCRIPTION OF THE DRAWINGS

Preferred embodiments of the invention will now be described, by way of examples only, with reference to the accompanying drawings in which:

FIG. 1 is a perspective side view of a first embodiment of circumcision device;

FIG. 2 is a perspective rear view of the device shown in FIG. 1;

FIG. 3 is a further perspective side view of the device shown in FIG. 1;

FIG. 4 is a perspective front view of the device shown in FIG. 1;

DETAILED DESCRIPTION OF THE PREFERRED EMBODIMENTS

Figure 7:
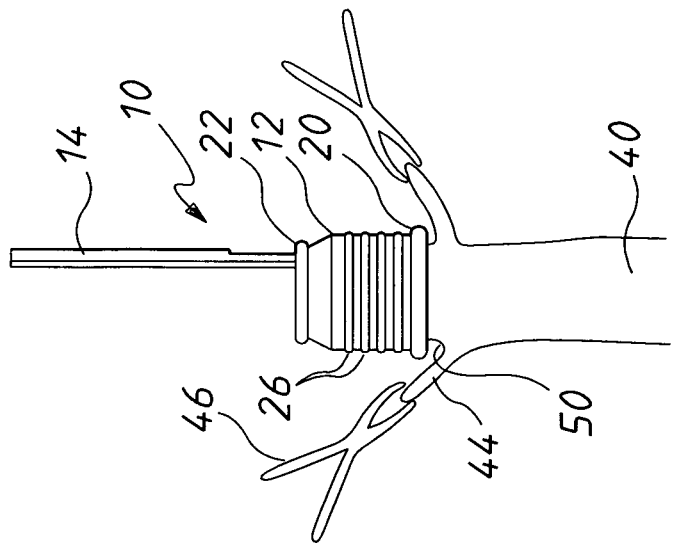
FIGS. 5 to 10 show sequentially the use of the device shown in shown in FIG. 1 during a circumcision procedure.

FIGS. 1 to 4 show a first embodiment of a single use circumcision device 10. The device 10 includes a generally cylindrical body 12 to which is frangibly attached a handle 14. The body 12 and handle 14 are moulded as a single component from a medical grade plastics material able to withstand sterilization.

The body 12 is generally cylindrical in shape and includes a proximal end 16 and a distal end 18. The proximal end 16 includes a first outwardly protruding peripheral flange 20. A second outwardly protruding peripheral flange 22 is provided adjacent to the distal end 18. The first flange 20 has a larger diameter than the second flange 22.

The body includes a cylindrical part 24 stemming from the first flange 20 which includes 4 outwardly protruding peripheral ribs 26. The cylindrical part 24 is connected to the second flange 22 via a tapering part 28.

As best shown in FIGS. 3 and 4 the interior of the cylindrical part 24 and tapered part 28 form an inwardly concave recess 30.

The device 10 is available in 9 sizes. In the device 10 shown in FIGS. 1 to 4, the recess 30 has an internal diameter of about 13 mm. The external diameter of the body 24 between the ribs 26 is about 14 mm. The cylindrical part 24 of the body 12 is about 16 mm in length. The handle 14 is approximately 35 mm in length. The first flange is about 2 mm thick, the second flange 22 is about 1.5 mm thick and the ribs 26 are about 1 mm thick. The ribs 26 are spaced apart by about 1 mm. It will be understood that these dimensions can be scaled up or down for other sizes of the device 10.

Figure 5:
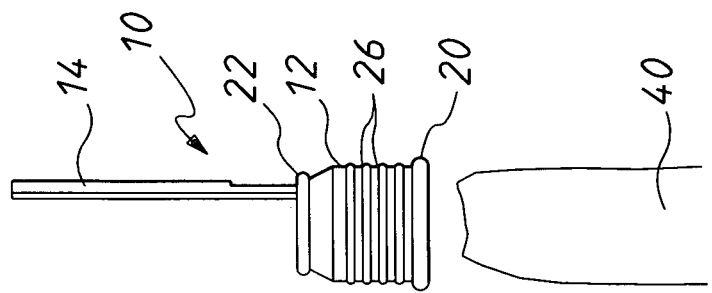

The use of the device 10 in a circumcision procedure shall now be described with reference to FIGS. 5 to 10. The device 10 is supplied in a sterilized blister pack (not shown). As shown in FIG. 5, the appropriate size of device 10 is selected, to suit the size of a penis 40 to be circumcised, and removed from the blister pack.

Figure 6:
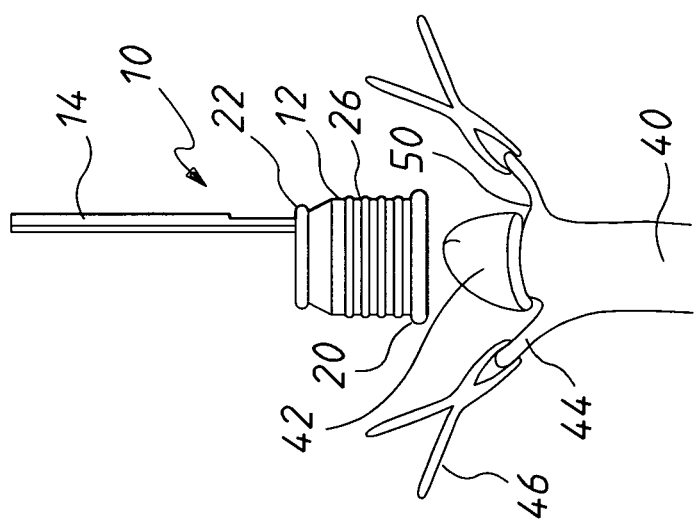

As shown in FIG. 6, the adhesions between glans 42 and foreskin 44 are divided with a probe and the foreskin 44 is then cut longitudinally to allow it to be retracted to expose the glans 42.

Figure 10:
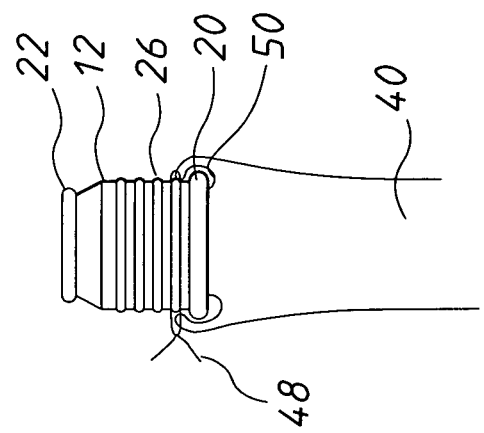

As shown in FIG. 7, the device 10 is then applied to the glans 42 of the penis, with the body 12 completely covering the glans 42. Put another way, the glans is completely received within the recess 30. The body 12 covers the entire glans 42, which is inserted up to the coronal sulcus. This ensures that proximal migration is not possible as the flange 20 around the proximal opening is wedged between the coronal sulcus, the foreskin 44 and the ligature 48. (as seen in FIGS. 8, 9 and 10).

Figure 8:
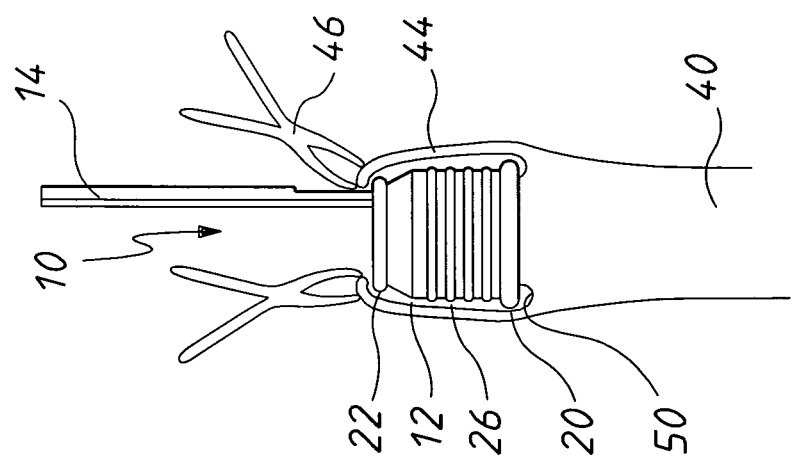

As shown in FIG. 8, the foreskin 44 is then send stretched over the exterior of the body 12 using clamps 46.

Figure 9:
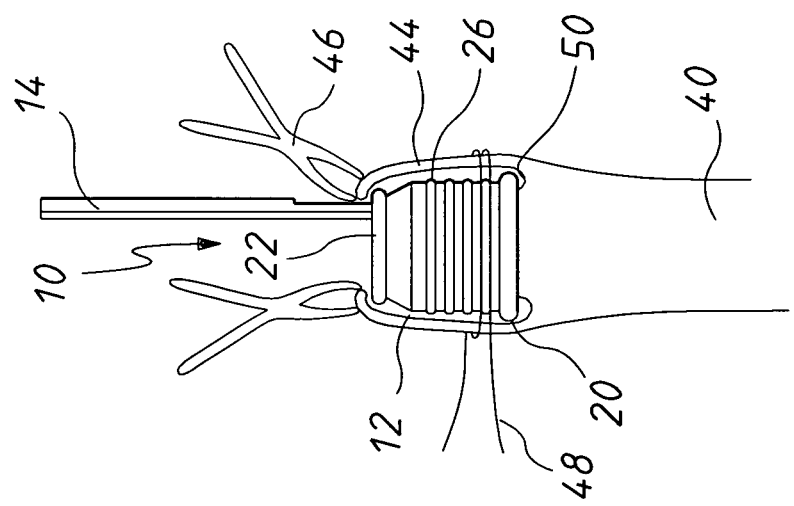

As shown in FIG. 9, a ligature 48 is tightly tied around the foreskin 44 crushing it against the exterior of the body 12. The body 12 covers the entire glans 42, which is inserted into the recess 30 up to the coronal sulcus 50. This ensures that proximal migration is not possible as the flange 20 around the proximal opening is wedged between the coronal sulcus 50, the foreskin 44 and the ligature 48 (as seen in FIGS. 8, 9 and 10). The surgeon is able to determine where to apply the ligature along the exterior of the body 12 by feeling the flange 20 and also the ribs 26 through the foreskin 44. The positioning of the ligature 48 and thus the amount of the foreskin 44 being removed in the circumcision procedure can thus be accurately determined, allowing the surgeon to select o either what is termed a 'tight' circumcision (i.e. a relatively large amount of foreskin removal) or a 'loose' circumcision (i.e. a relatively small amount of foreskin removal) or some level therebetween. Once the ligature 48 has been securely tied the excess skin protruding beyond the ligature 48 is trimmed off and the handle 14 is broken away from the body 12. The body 12 typically falls off in 3 to 7 days leaving a circumferential wound that heals over the following week.

The device 10 provides several advantages. Firstly, the glans of the penis is substantially completely covered (i.e. received within the recess 30), thereby protecting it from damage which may be caused by an incorrectly positioned ligature or a scalpel error.

Secondly, the position of the first flange 20 and thus the position of the body 12, can be easily determined by the surgeon by feeling the flange 20 through the foreskin. This reduces the likelihood of the ligature slipping over and off the proximal end of the device 10 and injuring the glans or remainder of the penis.

Thirdly, the second flange 22 at the distal end of the body provides an easily recognisable guide to the surgeon as to the end of the body. This advantageously reduces the possibility of the ligature being positioned (incorrectly) at a position where it may slip distally.

Fourthly, the ribs 26 serve as indicators as to the distance from the first flange 22 allowing the surgeon to easily and accurately determine a preferred position for the ligature and therefore the preferred amount of circumcision.

Fifthly, the groove created between each adjacent pair of ribs 26 improves the security of the location of the fastened ligature.

Sixthly, once the device 10 is in positioned on the glans, there is no tension in the foreskin attempting to pull the device 10 proximally. This is in contrast to the PLASTIBELL device, which the foreskin has to be pulled towards, creating an elastic tension attempting to pull the PLASTIBELL device proximally. The device 10 needs no pulling of the foreskin, thus removing the possibility of proximal migration occurring and avoiding injury.

Finally, the device 10 is used in a generally similar manner to the PLASTIBELL device, and therefore requires only minimal training before use.

Figure 11:
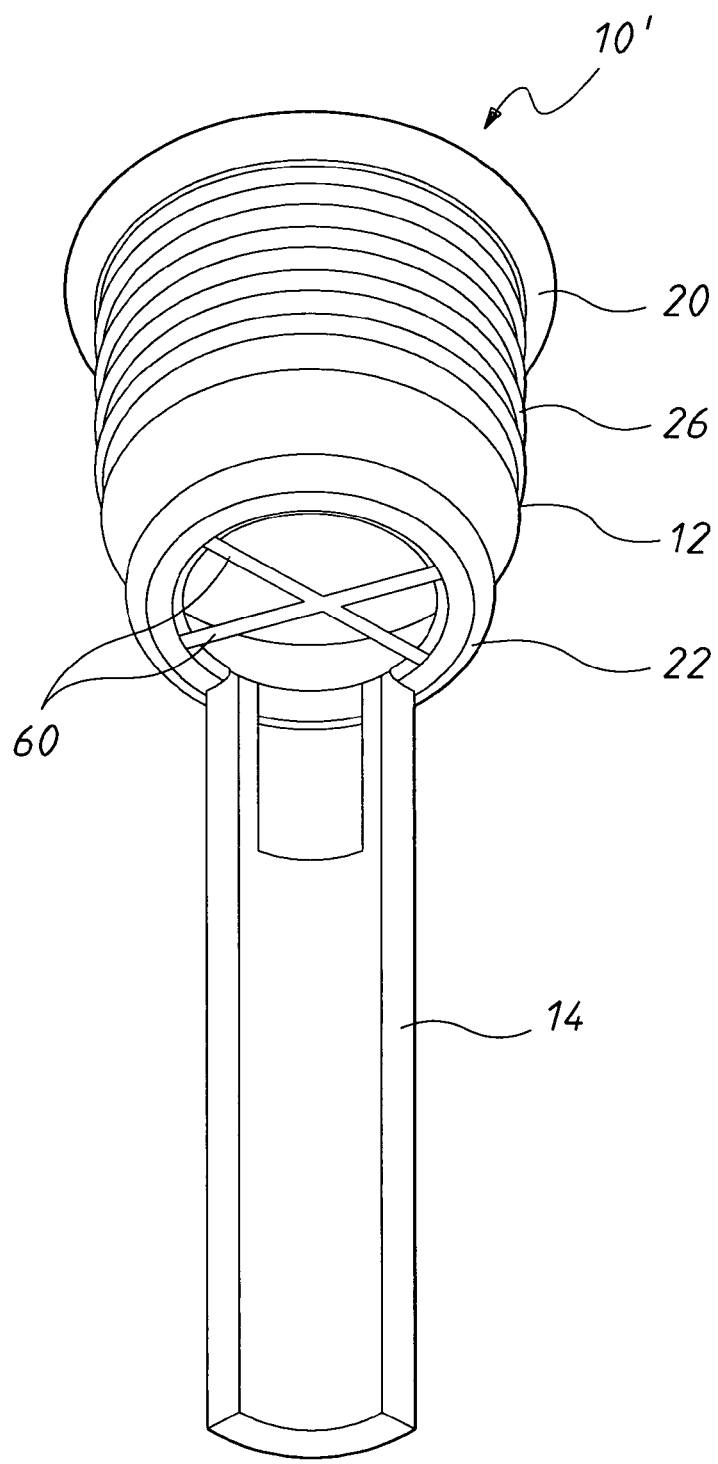
FIG. 11 is a perspective rear view of a second embodiment of circumcision device.

A second embodiment of circumcision device 10' in shown in FIG. 11. The device 10' is similar in construction and use to the device 10 previously described, except that it also includes two strips 60 across the opening within the second flange 22. The strips 60 ensure that proximal migration of the penis through the device 10' does not occur, by blocking the glans from sliding through the opening.

Figure 13:
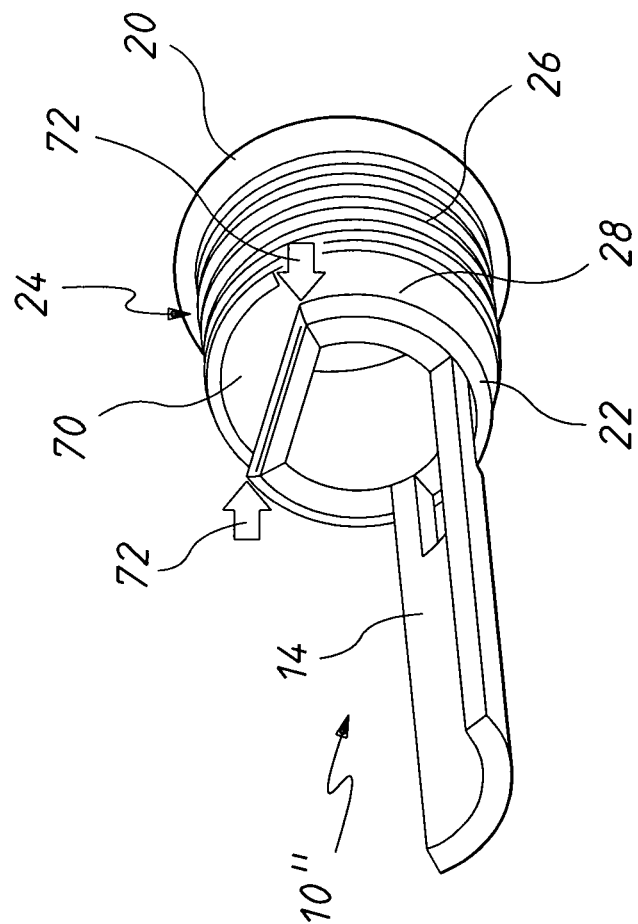
FIG. 13 is a perspective side view of the circumcision device shown in FIG. 12.
Figure 12:
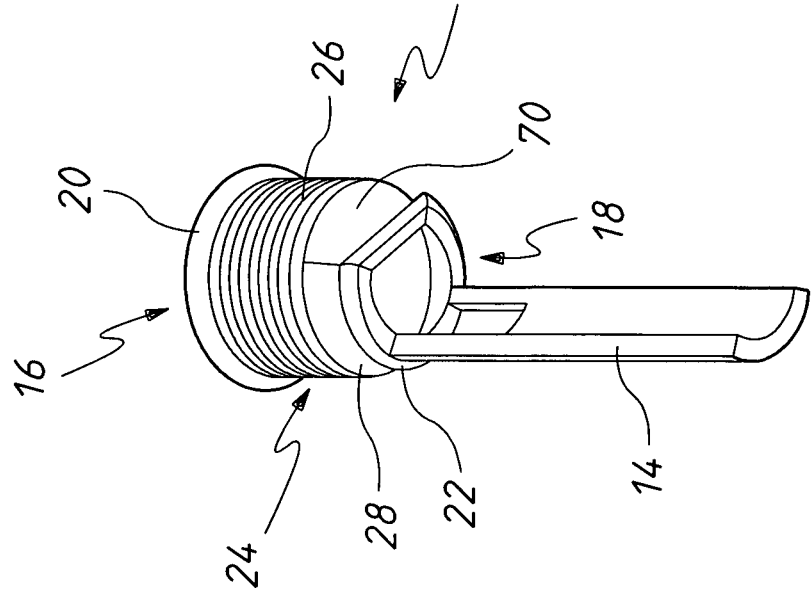
FIG. 12 is a perspective rear view of a third embodiment of circumcision device.

A third embodiment of circumcision device 10" in shown in FIGS. 12 and 13. The device 10" is similar in construction and use to the device 10 previously described, except that the tapering part 28 includes a chordal region 70. The chordal region 70 provides locations, indicated by arrows 72, in which pincers used to hold the foreskin can easily attach to, in comparison to having a tapering part with a circular cross section. This makes it easier for the surgeon to position the pincers during the circumcision procedure.

Figure 14:
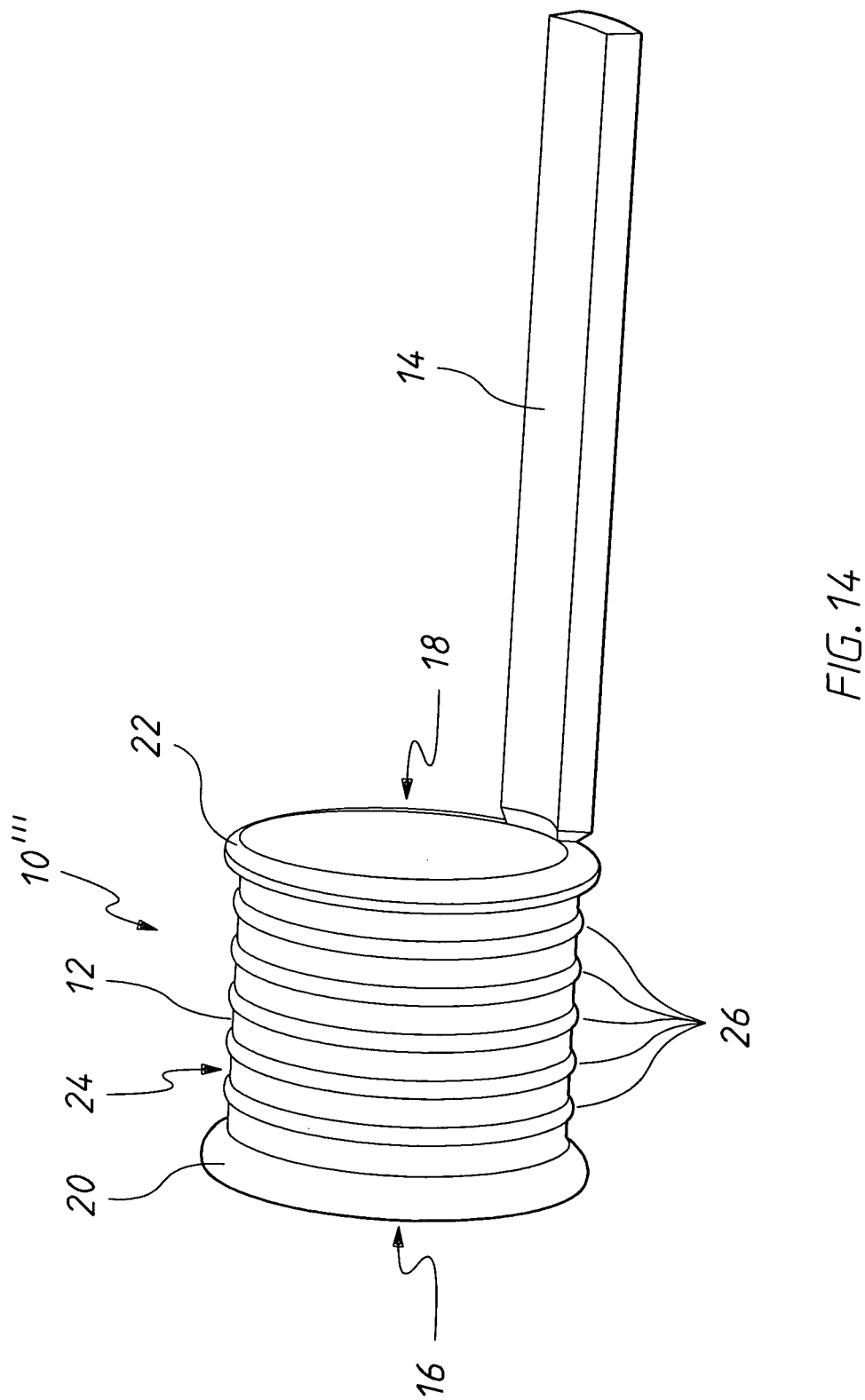
FIG. 14 is a perspective rear view of a fourth embodiment of circumcision device.

A fourth embodiment of circumcision device 10''' in shown in FIG. 14. The device 10''' is similar in construction and use to the device 10 previously described, except that the tapering part 28 is omitted, the body 12 is cylindrical and it has five of the ribs 26. This tapering part 28 is omitted to eliminate the (minute) risk of this part causing any chance of ischemia to the glans 42. The region where the handle 14 meets the cylindrical part is also designed to ensure the stress is concentrated where the handle meets the cylindrical part when the surgeon applied a force to break the handle off. This ensures a clean break, without sharp edges, when the handle 14 is to be broken off the body 12 post-circumcision.

Although the invention has been described with reference to preferred embodiments, it will be appreciated by those persons skilled in the art that the invention may be embodied in many other forms. For example, the device can include a third peripheral flange between the first and second flanges, which serves to act as a guide for a medium amount of skin removal. The length of the tapered part can also be increased to provide a narrower distal opening within the second flange. This will also prevent the glans from passing through the distal opening, whilst allowing urination. Alternatively, the tapered part can be deleted such that the cylindrical part extends between the first and second flanges. This ensures that, even if the glans does slide through the cylindrical part, there will be no harm to the glans.

The invention claimed is:

1. A circumcision device including:
   a proximal end;
   a distal end;
   an inner recess opening from the proximal end toward the distal end and adapted to receive substantially all of a glans of a penis therein; and
   an outer surface including a plurality of indicators in the form of four or more outwardly protruding peripheral ribs spaced apart from the proximal end, being configured to provide securement of a foreskin to the outer surface by a ligature,
   wherein, in use, a foreskin is pulled over the outer surface from the proximal end toward the distal end until the foreskin reaches a predetermined one of the indicators, thereby providing a visual guide to the level of circumcision and wherein the device includes a first outwardly protruding peripheral flange about the proximal end and wherein the plurality of indicators are about 1 mm thick and spaced apart by about 1 mm.

2. The circumcision device as claimed in claim 1, wherein the device also includes a second outwardly protruding peripheral flange about the distal end.

3. The circumcision device as claimed in claim 2, wherein the first flange is larger in diameter than the second flange.

4. The circumcision device as claimed in claim 1 wherein the device preferably includes a generally cylindrical body.

5. The circumcision device as claimed in claim 4, wherein the device includes a handle, frangibly attached to the body.

6. The circumcision device as claimed in claim 5, wherein the handle is adjacent the distal end.

7. The circumcision device as claimed in claim 4, wherein the inner recess opening is formed within the body.

8. The circumcision device as claimed in claim 7, wherein the inner recess opening is inwardly concave.

9. The circumcision device as claimed in claim 4, wherein the ribs are longitudinally spaced apart.

10. The circumcision device as claimed in claim 4, wherein the ribs are longitudinally equally spaced apart.

11. The circumcision device as claimed in claim 4, wherein the plurality of indicators includes five or more ribs.

12. The circumcision device as claimed in claim 1, wherein the device further comprises a generally cylindrical body that includes a tapered part adjacent the distal end.

13. A circumcision device including:
    a proximal end;
    a distal end;
    an outer surface including a plurality of indicators in the form of four or more outwardly protruding peripheral ribs spaced apart from the proximal end;
    an inner recess opening from the proximal end toward the distal end and adapted to receive substantially all of a glans of a penis therein; and
    the plurality of indicators adjacent to a first outwardly protruding peripheral flange about the proximal end,
    wherein the first outwardly protruding peripheral flange is about 2 mm thick and configured to prevent proximal migration of the circumcision device with respect to the penis when a foreskin of the penis is secured distally past the first flange and when substantially all of a glans of a penis is inserted in the inner recess opening, and wherein the device also includes a second outwardly protruding peripheral flange about the distal end that is about 1.5 mm thick.

14. The circumcision device as claimed in claim 13, wherein the first flange is larger in diameter than the second flange.

15. The circumcision device of claim 13, wherein the inner recess opening is the same diameter at the proximal end as at the distal end.

16. The circumcision device as claimed in claim 13, wherein the plurality of indicators includes five or more ribs.

* * * * *